United States Patent [19]

Shoher et al.

[11] Patent Number: 5,593,305
[45] Date of Patent: Jan. 14, 1997

[54] MOLDABLE DENTAL COMPOSITION

[76] Inventors: Itzhak Shoher, 50 Shlomo Hamelech St., Tel Aviv; Aharon E. Whiteman, J. L. Peretz St., 13 Petach Tikvah, both of Israel

[21] Appl. No.: 229,358

[22] Filed: Apr. 18, 1994

Related U.S. Application Data

[63] Continuation-in-part of Ser. No. 55,326, May 3, 1993, abandoned, which is a continuation-in-part of Ser. No. 887,245, May 19, 1992, Pat. No. 5,234,343, which is a continuation of Ser. No. 801,028, Dec. 2, 1991, abandoned.

[51] Int. Cl.⁶ .................................................. A61C 5/08
[52] U.S. Cl. ...................... 433/218; 433/223; 433/228.1; 29/896.1; 428/212; 75/228
[58] Field of Search .................................. 433/213, 214, 433/218, 223, 228.1, 215; 75/228; 29/160.6; 428/212

[56] References Cited

U.S. PATENT DOCUMENTS

| | | | |
|---|---|---|---|
| 4,355,980 | 10/1982 | Dwight | 433/228.1 |
| 4,426,404 | 1/1984 | Shoher et al. | 433/223 |
| 4,468,251 | 8/1984 | Hausselt et al. | 433/218 |
| 4,676,751 | 6/1987 | Shoher et al. | 433/218 |
| 4,698,021 | 10/1987 | Shoher et al. | 433/218 |
| 4,814,008 | 3/1989 | Shoher et al. | 433/207 |
| 4,846,718 | 7/1989 | Rieger | 433/218 |
| 4,940,637 | 7/1990 | Shoher et al. | 433/218 |
| 4,978,298 | 12/1990 | Eliasz | 433/213 |
| 4,990,394 | 2/1991 | Shoher et al. | 433/228.1 |
| 4,997,699 | 3/1991 | Shoher et al. | 428/212 |
| 5,094,689 | 3/1992 | Stuemke et al. | 106/35 |

*Primary Examiner*—Cary E. O'Connor
*Attorney, Agent, or Firm*—E. Lieberstein

[57] ABSTRACT

A moldable dental composition including high-fusing temperature metal particles and a binder comprising wax preferably in a concentration of above at least twenty percent (20%) of the composition. The high-fusing temperature metal particles should have an irregular nonspherical geometry and a thin cross-sectional average thickness. The moldable dental composition may also contain low fusing temperature metal particles for enhanced wetting of the high fusing metal particles during heat treatment at a heat treatment temperature which will substantially melt the low fusing metal particles. However it is not essential to the subject invention for the composition to contain low fusing metal particles.

19 Claims, 3 Drawing Sheets

MOLDABLE DENTAL COMPOSITION

FIELD OF THE INVENTION

This invention is a continuation-in-part of U.S. Ser. No. 08/055,326 filed May 3, 1993, now abandoned which in turn is a continuation-in-part of U.S. Ser. No. 07/887,245 filed May 19,1992, now U.S. Pat. No. 5,234,343, which is a continuation of Ser. No. 07/801,028 filed Dec. 2,1991 now abandoned and relates to a moldable dental material composition.

BACKGROUND OF THE INVENTION

A metal coping is used in dentistry in the construction of a dental crown and bridge. The metal coping functions as the understructure of the crown and is usually covered, for reasons of aesthetics, with a fired-on coating of ceramic porcelain composition or an acrylic. The metal coping supports the coating and provides the required structural strength and rigidity for the restored tooth to resist the forces of mastication.

The customary practice is to cast the metal coping from an investment of a wax or plastic pattern of the tooth to be restored. The restoration formed using this procedure is conventionally referred to as a cast metal restoration. A metal coping has recently been developed for constructing a porcelain to metal crown which does not require waxing, investing or casting. The coping is formed from a prefabricated metal foil arranged in a prefolded configuration, with a plurality of foldable sections, as described in more detail, in U.S. Pat. No. RE. 33,099, which issued to Applicant on Oct. 24, 1989. An alternative method of forming a dental coping from a metal foil is taught by Applicant in U.S. Pat. No. 4,861,267, which issued on Aug. 29, 1989. In each instance, the starting material for forming the coping is a solid metal foil formed from a lamination of solid metal layers, each of a precious metal.

As an alternative to the use of a prefabricated metal foil, Applicant developed a dental material composition, as disclosed in U.S. Pat. No. 4,997,694, which is capable of being molded into a desired shape, which is self-supporting in the molded configuration, and which will retain the shape in which it is molded under heat treatment. The dental material, as taught in the aforementioned patent, the disclosure of which is herein incorporated by reference, comprises a metal composition, including particles of high-fusing temperature metal having a melting temperature above a preselected heat-treatment temperature, and metal particles of a low-fusing temperature, which substantially melts during heat treatment at such heat-treatment temperature to form a porous, sponge-like structure, with the high-fusing temperature metal particles interconnected by the melted, low-fusing temperature metal. Applicant further teaches in U.S. Pat. No. 4,990,394, that the porous, sponge-like structure should provide a total void volume of between twenty (20%) to eighty percent (80%).

SUMMARY OF THE INVENTION

A dental composition has been discovered which can be molded with little effort to form a dental coping, dental crown or filling. The composition containing wax forms a material which may be worked on a refractory die, dies made of other materials or in the mouth. The procedure for forming a metal coping, repairing a dental restoration or filling a tooth can be readily practiced either at the dental laboratory or by the dentist in the dental office.

The moldable dental composition of the present invention comprises: high-fusing temperature metal particles and a binder comprising wax wherein said high-fusing particles have an irregular non-spherical geometry and a thin cross-sectional average thickness with at least 50% of the particles having an average thickness of less 1.5 microns determined by measuring the surface area of each high fusing particle in a plane containing the largest two dimensional image of the particle, computing the total surface area of all of the high fusing particles and dividing the cumulative surface area of the high fusing particles which are below 1.5 microns in average thickness by the computed total surface area. The dental composition should preferably also contain low fusing metal particles having a melting temperature below the melting temperature of the high fusing metal particles. The longest dimension of the high fusing particles should preferably not exceed an average of eighty (80) microns.

The moldable dental composition of the present invention also comprises high-fusing temperature metal particles and a binder of wax with said high-fusing particles having an irregular non-spherical geometry and a thin cross-sectional average thickness wherein at least 30% of the high fusing metal particles are unidirectionally oriented in parallel to the surface of the material. The unidirectionally oriented high fusing flakes form laminations which are parallel to the surface of the dental material.

BRIEF DESCRIPTION OF THE DRAWINGS

Additional advantages of the present invention will become apparent from the following detailed description of the invention when read in conjunction with the accompanying drawings of which.

DETAIL DESCRIPTION OF A PREFERRED EMBODIMENT OF THE INVENTION

Figure 1:
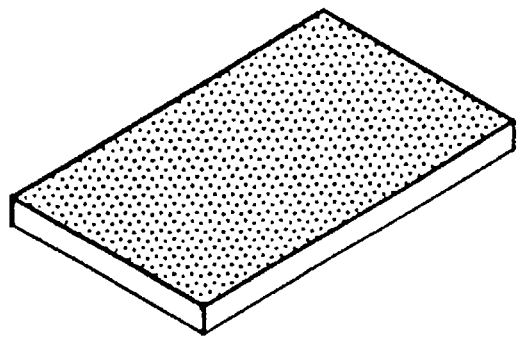
FIG. 1 is a perspective view of a compacted strip formed from the dental composition of the present invention.

The dental material of the present invention is a moldable composition formed preferably from a mixture of particles of high as well as low-fusing temperature metals and a binder, preferably of a wax composition. The concentration of the binder is preferably between twenty percent by volume of the mixture, and up to eighty percent. The wax binder permits the material to be heat-treated for forming a porous sponge-like structure having multiple voids uniformly distributed throughout the structure and a void volume of at least twenty percent. The uniformity and homogeneity of voids in the porous structure is a desirable feature which permits the flow of filler to flow uniformly throughout the void structure. The voids formed in the heat-treated material on a volume basis ("void volume") may range between twenty to eighty percent by volume, and preferably between forty and sixty-five percent by volume. Upon heat treatment the binder volatizes, leaving a porous metal structure with essentially little or no shrinkage.

In accordance with the present invention, a filler material is melted into the voids of the heat-treated porous structure to densify the structure for forming the final dental restoration. The porous metal structure is first shaped into a desired configuration for forming a dental restoration before the filler material is added. The filler material may be any suitable ceramic or metal composition, preferably a precious metal composition. It is a preferred embodiment of the present invention to form a matrix of particles of filler material, which are mixed with a wax component in a concentration similar to the binder concentration used to form the porous structure. A minimum wax concentration of at least about twenty percent by volume is preferred, and up to seventy-five percent by volume. The filler particles may be an alloy of at least fifty percent by weight of gold with other metals such as silver, copper, zinc, aluminum, magnesium, gallium, indium, or any of the platinum group metals and/or elements from the third or fourth groups of elements of the periodic table of elements to form a melting gradient during melting of the filler material, such that the filler particles melt in a preferred sequence. A maximum of up to seven percent (7%) silver and a maximum of up to ten percent (10%) of other elements is preferred. Fluxes may also be included in the filler material.

The wax in the binder is not critical to the invention, and any natural wax, mineral wax, or organic wax composition may be used which is relatively soft and tacky. The binder should melt relatively cleanly without leaving a significant residue. The melting temperature of the binder must be below the melting temperature of the low-fusing temperature metal particles, and below the melting temperature for the filler material. Moreover, the high- and low-fusing temperature metal particles should combine readily with the binder at room temperature to form a mixture with a uniform distribution of metal particles and binder. At least 20% of the composition should consist of wax. A direct correlation exists between the wax concentration and the void volume of the porous structure after heat treatment.

The high-fusing temperature metal component is critical to the composition and may be a single metal or metal alloy, preferably of precious metals such as platinum and palladium in any desired proportion to one another from zero to one hundred percent and may include gold in any desired concentration. Additional constituents may be added such as Ag, Cu, Mg, Al, Zn, and other metals of the platinum group of elements of the third and fourth group of elements. The total weight percent of the elements other than gold, silver, and the platinum group metals should not exceed ten percent. Gold may be added in any proportion to the highfusing temperature metal component to increase the affinity of the highfusing temperature metal component to the low-fusing temperature metal component or to itself in the absence of the low fusing component. In the latter instance gold may represent the major constituent of the high fusing metal composition and depending upon its concentration will lower the melting temperature of the high fusing component to as low as 900°–950° C.

When the high fusing particles are selected of appropriate geometry and size as will be explained hereafter the composition may be limited to only high fusing metal particles i.e. the low fusing metal particles may be excluded from the composition. However the preferred composition will include low fusing metal particles to enhance the wetting of the high fusing particles during heat treatment. The particles of low-fusing temperature metal are composed preferably of gold or a gold alloy, with gold as the major constituent. The preference for gold as the major constituent of the low-fusing component is based on its known characteristics of workability, biocompatibility, non-oxidizing properties and color. The low fusing metal particles must, of course, have a melting temperature below that of the high fusing metal particles.

The shape of the high-fusing metal particles has been found to be important to maintain dimensional control over the voids formed between the high-fusing particles during heat treatment. Irregular shaped particles, in the form of flakes i.e. platelets function best. The size and dimensions of the irregular, flake-like particles play an important function. In fact when the high fusing particles are substantially all of irregular geometry and of preferred thickness and/or orientation as will be elaborated upon hereafter it has been discovered that the moldable dental composition may exclude low fusing metal particles. The very thin platelets of high fusing particles interleave one another to provide sufficient mechanical integrity to form a porous structure during heat treatment without the presence of low fusing particles and retains its structure after heat treatment with minimal shrinkage. It is postulated that even without low fusing particles the heat treatment operation forms localized autogeneous joints which maintains the structural integrity of the porous structure after heat treatment. However, the porous structure formed with the use of low fusing particles as part of the composition is preferred. The platelet geometry and interleaving is demonstrated in FIGS. 5–7 inclusive.

At least 50% of the high fusing particles should have a thin, cross-sectional, average thickness of less than about 1.5 microns determined by measuring the surface area of the largest two dimensional image of each high fusing particle, computing the total surface area of all of the high fusing particles and dividing the cumulative surface area of the high fusing particles which are below 1.5 microns in average thickness by the computed total surface area. The surface area calculation is a simple two dimensional measurement of the area circumscribing the flat planar surface containing the largest two dimensional image of each particle. If the planar geometry of the particle were rectangular the surface area would simply be the length times the width. As an illustration assume a flake geometry of 5μ(long)×10μ(wide)×3 microns thick. The largest two dimensional surface area is 5μ×10μ. For a second illustration assume a geometry of 20μ(long)×5μ(wide)×1μ(thick). Again the largest two dimensional surface area is 20μ×5μ. As a third example assume a flake geometry of a ball having a diameter of 20 microns. A two dimensional projected image would be a circle having a surface area of $\pi r^2$ or $\pi 100$. The necessity for taking a projected image of the largest two dimensional surface is based upon undulations and irregularities in the flake surfaces which would otherwise complicate the surface area calculation. The cumulative total of the surface area for all of the particles is preferably determined by statistical analysis. There are commercial analytical instruments and techniques available which may be used for computing the surface area of the particles. Preferably most of the particles will have a very thin cross sectional thickness of less than about 1.5 microns. However, since it is possible to break larger particles into many smaller particles it is necessary to make a surface area measurement to determine if at least 50% of the total population of the high fusing particles in the composition are of proper thickness.

As explained above by appropriate selection of the geometry and size of high fusing particles the low fusing particles may be entirely eliminated from the composition. A composition without low fusing particles may be desirable for forming the abutments in bridgework. However the use of low fusing particles is generally preferred and the best results are achieved using a mixture of both high and low fusing particles in a wax binder with the high fusing particles having the desired geometry and size. When using a mixture of metal particles the relative volume percent of the low fusing metal particles in the composition should lie in a range of from about 40% to about 65% for most applications and preferably between 42% and 55% by volume. In general, if the volume percent of the high-fusing component in the composition is too large, particularly for a high fusing component of high melting temperature, there may not be adequate wetting between the high-fusing particles during heat treatment, and if the volume percent of the high fusing component is too small too much wetting will occur and the structure will collapse, i.e., become too dense. As the average thickness of the high fusing particles in the total composition decreases to below 1.5 microns the volume percent of the low-fusing component within the above range may increase particularly for thicknesses below 0.5 microns.

In general, the longest dimension should not exceed an average of preferably about eighty (80) microns and should preferably range from over two (2) to fifty (50) microns, with the average shortest dimension in a range of preferably between one (1) and twenty-five (25) microns in length, although the absolute values of these dimensions are not particularly significant. The high-fusing particles may be longer or equal in size to the low-fusing particles (with the low fusing particles preferably measured by its diameter since the low-fusing particles are generally spherical).

Figure 5:
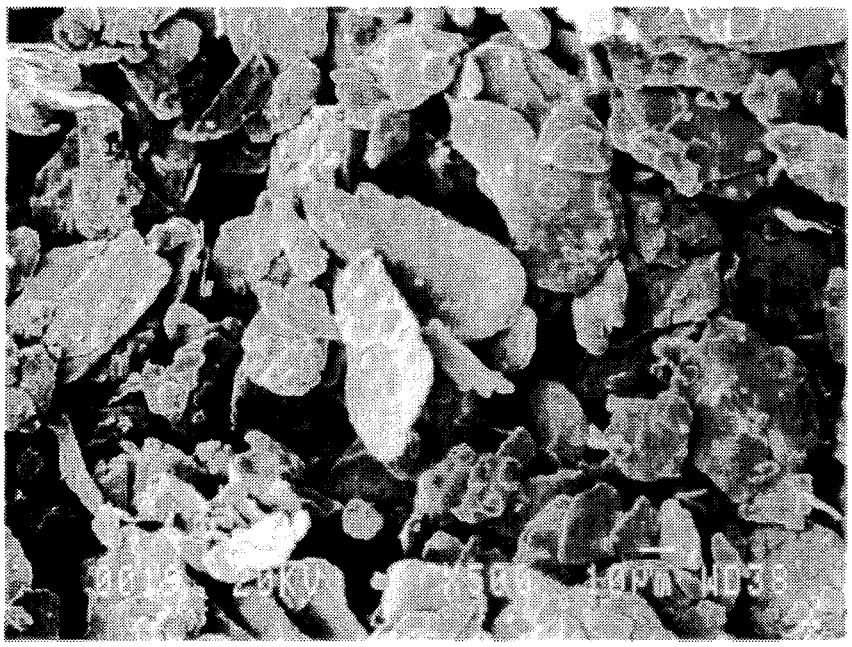
FIG. 5 is a photomicrograph of the dental composition of the present invention prior to heat treatment but after volatizing the wax and at a magnification of 500 times.
Figure 6:
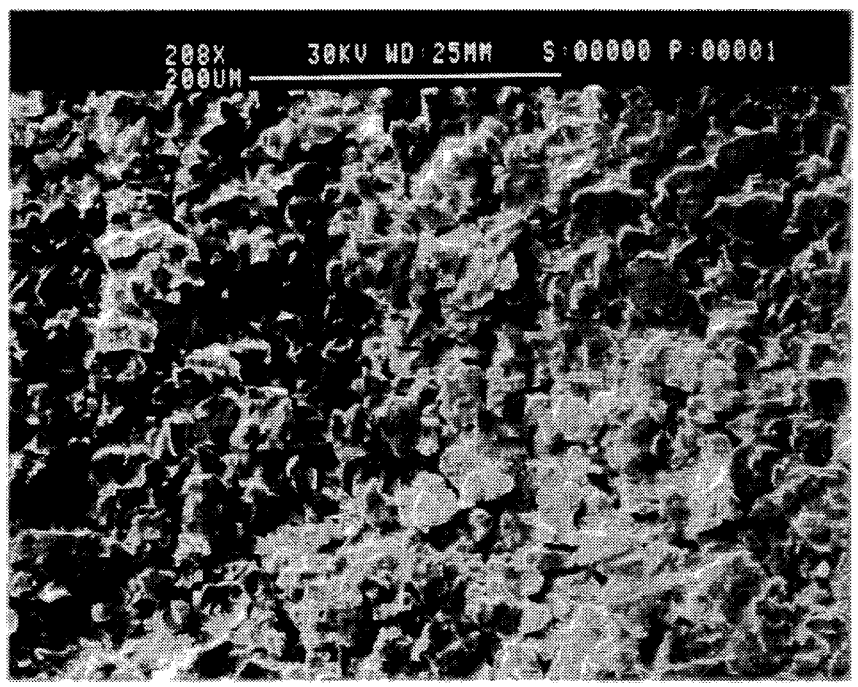
FIG. 6 is another photomicrograph of the dental composition after volatizing the wax prior to heat treatment at a magnification of 200 times.

When the high fusing metal particles possess a flake-like geometry and are very thin they overlap to form a lattice network of particles as shown in FIGS. 5 and 6. This assures adequate strength even when the composition is thinned down near the dental margin without flaking. The thin flakes also assures a compact, open-pore structure of uniform porosity, which also provides a greater reliability of dimensional control over the voids in the heat-treated structure. The strength of the heat treated structure is improved however when the high fusing particles are not randomly oriented in the wax binder. Preferably at least 30% of the high fusing particles should be unidirectionally oriented in parallel to one another to form laminations in a direction parallel to the surface of the material i.e. parallel to the longitudinal axis of the dental material. With this preferred orientation of high fusing flakes of thin cross sectional thickness the low fusing component may be omitted entirely or of low concentration. For this special case the integrity of the heat treated structure is dependent primarily upon the overlapping layered formation of the high fusing particles. It is also desirable to include in the composition independent of whether low fusing particles are omitted relatively finely divided carbonaceous particles preferably of activated carbon in a concentration typically between 0.005% and 1.0% by weight.

Figure 7:
FIG. 7 is another photomicrograph of the composition of FIG. 5 taken at right angles to the composition to illustrate the thickness of the particles at a magnification of 10,000 times.
Figure 8:
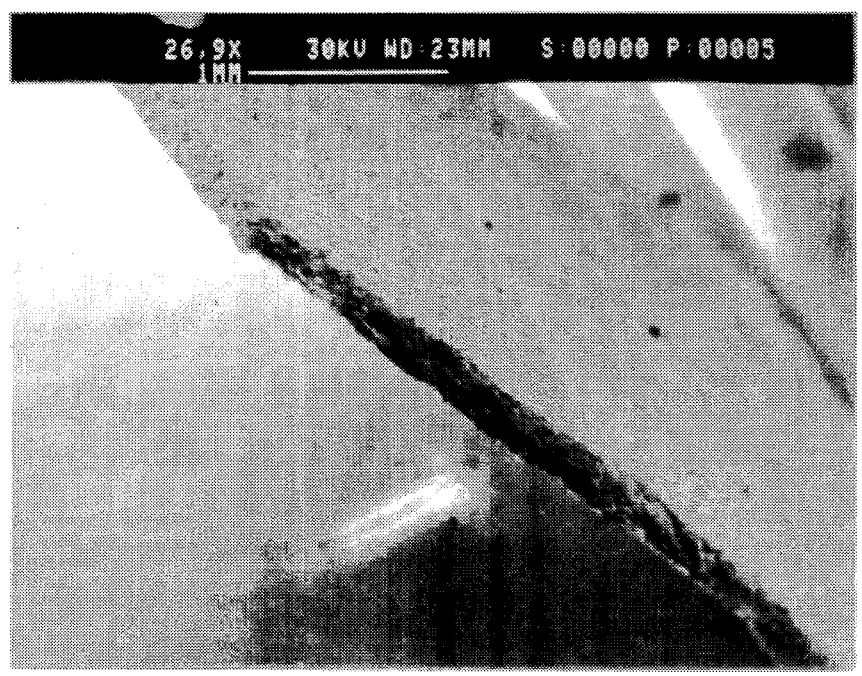
FIG. 8 is yet another photomicrograph of an edge of a typical high fusing metal particle to provide a visual indication of its geometrical shape and thickness relative to the planar surface containing the longest dimension.

FIGS. 5–7 illustrate the shape and orientation of the particles. and FIG. 8 illustrates the cross sectional thickness of the particles. The space and distribution of voids, i.e., capillary void network, is much more readily controlled using the above-described flake geometry and dimensions. There is a substantial direct correspondence between void volume and wax binder concentration for the composition of the present invention with substantial control over homogeneity in its porosity.

The composition should be heat treated at a temperature which will eliminate the wax binder, preferably without leaving a residue, and cause the low-fusing particles to melt to form a porous metal structure with a uniformly distributed void matrix.

In accordance with the preferred method of the invention, the base mixture of wax and high- and low-fusing temperature metal particles are compressed into a compacted strip, as shown in FIG. 1 in the form of a rectangular sheet, although any geometrical shape may be formed, including a cylindrical rod-like shape. The sheet thickness may lie between 50 and 1000 microns, depending upon the specific application, with a thickness between 100 to 500 microns preferred for forming a dental coping. The filler material and wax may, likewise, be compacted into a strip or other geometry, for ease of application to the porous structure formed from the base mixture.

Different metal-wax mixtures may be used to form laminated layers for special applications where, for example, it is preferable to have a variation in the void volume characteristic of the porous structure formed after heat treatment. For example, a compacted strip composed of two layers, as shown in FIG. 1 A, may be formed with one layer having twice as much wax as the other. This will result in a porous structure which has roughly twice the void volume in its exterior or interior, depending on whether the interior or exterior has the higher wax concentration. Moreover, the layer thickness may be varied and/or different metal alloy compositions may be used to form each layer. The number of layers in the strip, their composition, arrangement, and thickness can be used to predetermine the properties of the porous structure.

Figure 1A:
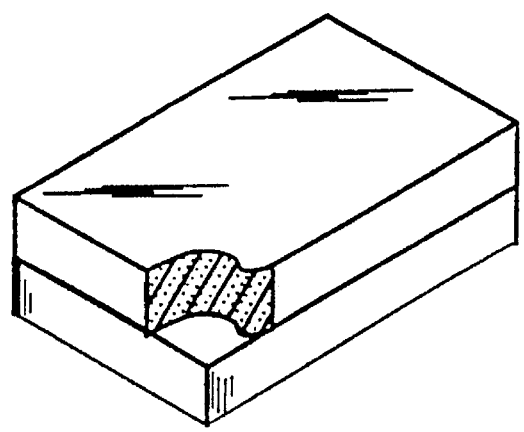
FIG. 1A is a view similar to FIG. 1 of a compacted strip formed of two layers.

The filler material-wax composition may also be formed into a compacted strip (not shown) or may be laminated over the strip of base material, similar to FIG. 1A. If they are preclad, it is still essential that the heat treatment be at a first temperature which will form a porous structure without melting the filler material. However, the wax component in each layer may be volatilized or be otherwise eliminated through melting. Thereafter, the heat treatment temperature may be raised to melt the filler material into the voids of the porous structure. Although the filler material should not melt or disturb the sintering process of the base material, components of the filler material, such as fluxes, binders, etc., may indeed melt into the porous structure during this first heat treatment.

When the porous sponge-like structure is formed from an independent strip of base material, the filler material may have a sintering temperature of more or less than that of the sintering temperature of the low-fusing temperature metal particles in the base material.

To form a coping from a strip of base material, the strip is preferably cut into pieces or sections which are applied to the surface of a die. The pieces are hand-molded, using pressure, with or without the use of an adhesive. The adhesive may be composed of a wax with a solvent and may include other components, such as other adhesive agents, fluxes, etc. Hand-molding is done with the aid of a spatula or other hand instrument. The carving of the base metal-wax material into a preferred shape may be done on a model and then removed, or supported in any other fashion, for heat treatment. The heat treatment may be done in a furnace or under a flame. The usual heat treatment temperature range for the base material is between 800° C. and 1200° C. Heat treatment must be conducted at a temperature below the melting temperature of the high fusing metal particles. The heat treatment of the filler material may also be done in a furnace or using a flame.

Figure 2:
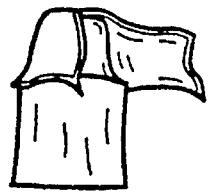
FIG. 2 is a transparency in perspective of the waxed coping hand-molded over the die of a prepared tooth, with the coping shown opened to illustrate thickness.
Figure 3:
FIG. 3 is a perspective of the metal coping formed on the die of FIG. 2 after heat treatment.
Figure 4:
FIG. 4 is an illustration in perspective of the finished dental coping of FIG. 3 upon removal from the die.

The pieces of wax-strip are easily shaped or carved into any desired geometry, as shown in FIG. 2, with little effort and require no expertise. The wax coping can have any thickness. The heat treatment may be carried out directly on the die, with the wax absorbed into the die, leaving a sponge-like structure, as shown in FIG. 3. As the temperature is raised to the sintering temperature, the wax burns out and the sinterization process forms the spongy structure. Filler material is then added to the porous structure and heat treated to form a dense solid coping, as shown in FIG. 4.

It should be understood that the dental material of the present invention can be used for repair work or to join two restorations at the interproximal. The repair work can be of a preformed metal restoration or of a cast metal restoration.

What is claimed:

1. A moldable dental composition for forming a porous structure upon heat treatment having a void volume of at least 20%, said composition comprising high-fusing temperature metal particles and a binder comprising wax wherein said high-fusing particles have an irregular non-spherical geometry and a thin cross-sectional average thickness with at least 50% of the high fusing particles having an average thickness of less than 1.5 microns determined by measuring The surface area of the largest two dimensional planar image of each high fusing particle, computing the total surface area of all of the high fusing particles and dividing the cumulative surface area of the high fusing particles which are below 1.5 microns in average thickness by the computed total surface area.

2. A moldable dental composition, as defined in claim 1, wherein said composition further comprises low-fusing temperature metal particles having a melting temperature below the melting temperature of the high fusing particles.

3. A moldable dental composition as defined in claim 2, wherein the longest dimension of said high fusing temperature metal particles is no longer than about eighty (80) microns.

4. A moldable dental composition as defined in claim 3 wherein at least 30% of the high fusing metal particles are unidirectionally oriented in parallel alignment with its longest dimension so as to form a layered structure upon heat treatment.

5. A moldable dental composition as defined in claim 4 wherein the low-fusing temperature metal component is between 40 to 65 percent by volume of said composition.

6. A moldable dental composition, as defined in claim 5 wherein the void volume of said porous structure is between 35 to 65 percent.

7. A moldable dental composition as defined in claim 6 wherein said longest dimension of each particle is in a range of above two (2) to eighty (80) microns.

8. A moldable dental composition as defined in claim 7 wherein the shortest dimension of each particle is in a range of between one (1) and twenty-five (25) microns.

9. A moldable dental composition as defined in claim 4 further comprising a second composition for densifying the porous metal structure formed upon heat treatment wherein said second composition comprises a mixture of particles of a filler material, having a melting temperature below the melting temperature of said high-fusing metal particles and wax, with said wax in a concentration of at least about thirty percent by volume of said second composition.

10. A moldable dental composition as defined in claim 9 wherein said second composition is gold or an alloy of at least fifty percent by weight of gold and a metal selected from the group consisting of other metals such as silver, copper, zinc, aluminum, magnesium, gallium, indium, or any of the platinum group metals and/or elements from the third or fourth groups of elements of the periodic table of elements.

11. A moldable dental composition, as defined in claim 10, further comprising a flux.

12. A moldable dental composition, as defined in claim 11, wherein the average size of said high-fusing metal particles are equal to or greater than the average size of the low-fusing metal particles.

13. A moldable dental composition, as defined in claim 9, wherein said second composition is in the form of a compacted strip.

14. A moldable dental composition, as defined in claim 4, arranged in the form of a compacted strip having a thickness of between 50 to 1000 microns.

15. A moldable dental composition, as defined in claim 14, wherein said thickness is between 150 to 500 microns for forming a dental metal coping from said strip.

16. A moldable dental composition, as defined in claim 15, wherein said mixture is formed into a strip having more than one layer, with each layer having a different wax concentration.

17. A moldable dental composition comprising high-fusing temperature metal particles and a binder comprising wax characterized in that said high-fusing particles have an irregular non-spherical geometry and a thin cross-sectional average thickness wherein at least 30% of the high fusing metal particles are unidirectionally oriented in parallel alignment with its longest dimension.

18. A moldable dental composition as defined in claim 17 further comprising carbonaceous particles preferably of activated carbon in a concentration between 0.005% and 1.0% by weight.

19. A moldable dental composition, as defined in claim 18, wherein said composition further comprises low-fusing temperature metal particles.

* * * * *